(12) United States Patent
Musa

(10) Patent No.: US 7,456,280 B2
(45) Date of Patent: Nov. 25, 2008

(54) MALEIMIDE RESIN WITH CYANURATE CORE

(75) Inventor: Osama M. Musa, Hillsborough, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 323 days.

(21) Appl. No.: 10/549,899

(22) PCT Filed: Jan. 16, 2004

(86) PCT No.: PCT/US2004/001192

§ 371 (c)(1),
(2), (4) Date: Sep. 16, 2005

(87) PCT Pub. No.: WO2005/077923

PCT Pub. Date: Aug. 26, 2005

(65) Prior Publication Data

US 2007/0232802 A1    Oct. 4, 2007

(51) Int. Cl.
*C07D 251/34* (2006.01)
(52) U.S. Cl. ............... 544/192; 544/221; 544/222
(58) Field of Classification Search ........ 544/192, 544/222, 221
See application file for complete search history.

(56) References Cited

U.S. PATENT DOCUMENTS

| | | | |
|---|---|---|---|
| 6,034,150 A | 3/2000 | Hoyle et al. | |
| 6,265,530 B1 | 7/2001 | Herr et al. | |
| 6,350,840 B1 | 2/2002 | Schultz et al. | |
| 6,369,124 B1 | 4/2002 | Hoyle et al. | |
| 6,410,611 B1 | 6/2002 | Sakurai et al. | |
| 2003/0087999 A1 | 5/2003 | Dershem et al. | |
| 2003/0109666 A1 | 6/2003 | Dershem et al. | |

FOREIGN PATENT DOCUMENTS

| | | |
|---|---|---|
| EP | 1 016 659 | 9/2003 |
| EP | 1 411 081 | 4/2004 |
| JP | 11352683 | 12/1999 |
| JP | 2001217262 | 8/2001 |
| JP | 2001348375 | 12/2001 |
| JP | 2003040939 | 2/2003 |
| JP | 2003327662 | 11/2003 |
| JP | 2004012671 | 1/2004 |
| WO | WO 92/07904 | 5/1992 |

OTHER PUBLICATIONS

Sukarai et al., JP 200340939-Part 1.*
Sukarai et al., JP 200340939-Part 2.*

* cited by examiner

*Primary Examiner*—Venkataraman Balasubramanian
(74) *Attorney, Agent, or Firm*—Jane E. Gennaro

(57) ABSTRACT

Isocyanurate compounds or resins have the structure (I) in which Y is an hydroxyl group —OH or a maleimide group Formula (II) provided that at least one maleimide group is present, and Q is any divalent organic moiety, aliphatic or aromatic.

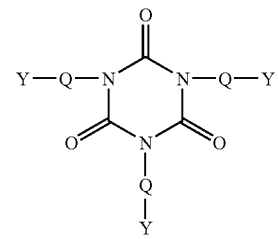

(I)

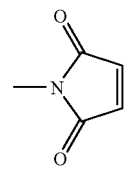

(II)

3 Claims, 1 Drawing Sheet

MALEIMIDE RESIN WITH CYANURATE CORE

FIELD OF THE INVENTION

This invention relates to maleimide compounds or resins that contain a cyanurate core and that are suitable for use as adhesives or encapsulants in semiconductor packages.

BACKGROUND OF THE INVENTION

Resins that have maleimide end groups and an aromatic core or an alkylene backbone are known in the art. Resins that have acrylate end groups and an isocyanurate core are known in the art. Such resins are useful as adhesives, encapsulants, and sealants. However, within the semiconductor industry, which has stringent requirements for the materials used in the fabrication of semiconductor packages, there is always a need for new resins with useful properties. The resins of this invention find utility due to improved adhesion and improved modulus at high temperature.

SUMMARY OF THE INVENTION

This invention is a compound having an isocyanurate core and one or more maleimide groups on the ends of hydrocarbon arms radiating from the core. The compounds have the structure:

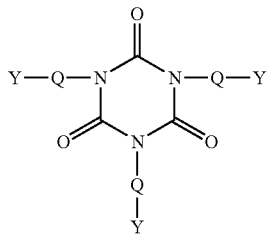

in which Y is an hydroxyl group —OH or a maleimide group

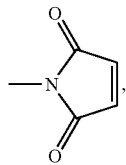

provided that at least one maleimide group is present, and Q is any divalent organic moiety, aliphatic or aromatic. The organic moiety may be linear or cyclic and contain carbon to carbon unsaturation or heteroatoms, such as, oxygen, nitrogen and sulfur. The organic moiety may also contain functional groups, such as, amide, carbamate, carboxyl, ester, thio, and urea groups. Exemplary Q groups are polyesters, polyurethanes, polysiloxanes, or simple alkylene or alkenylene moieties. The structure of the arms radiating from the core can be varied as suits the needs of the practitioner. Examples of the structure of the arms and synthetic methods are disclosed later in this specification.

DETAILED DESCRIPTION OF THE INVENTION

Figure 1:
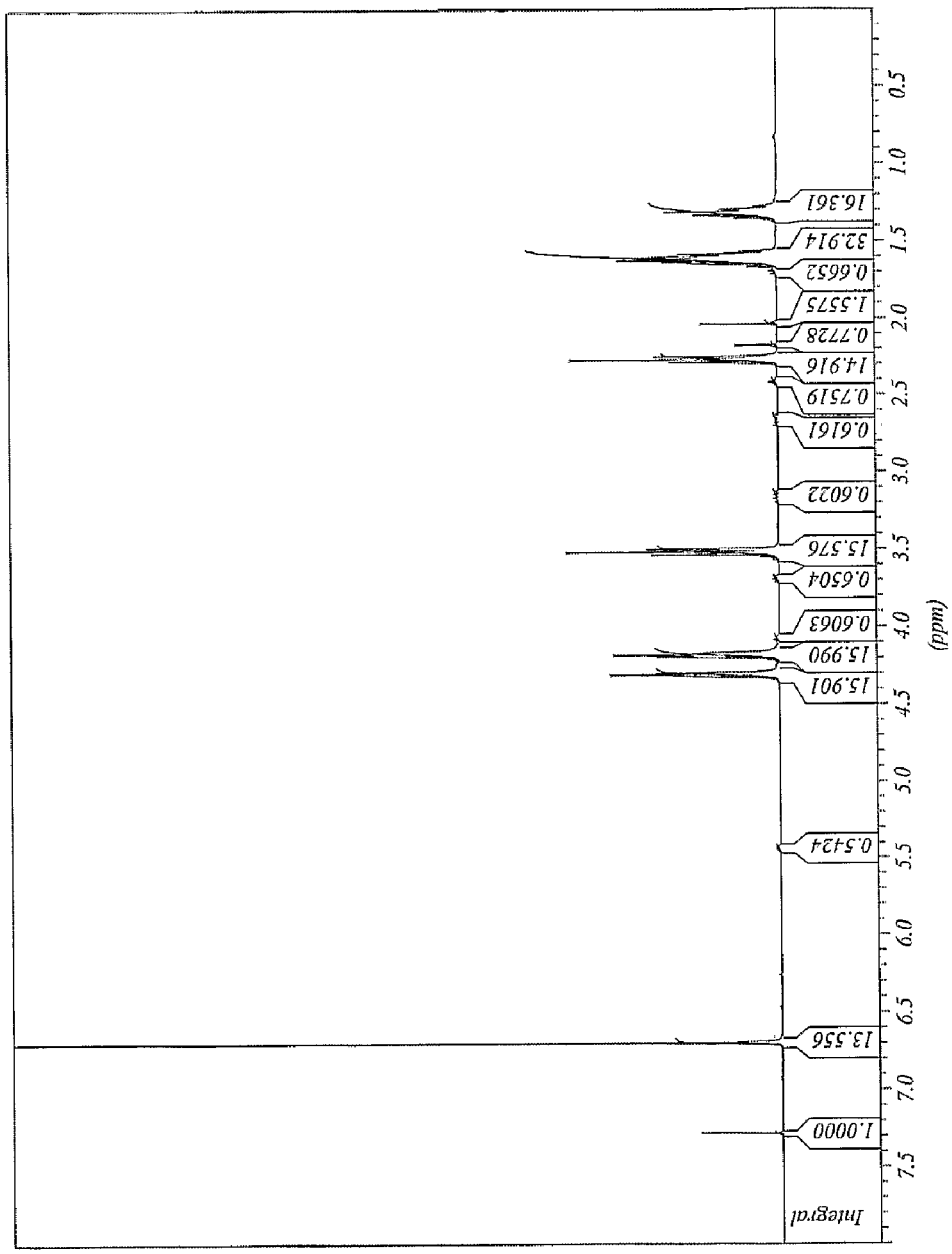
FIG. 1 is the NMR spectrum of Example 1.

The isocyanurate compounds used in the adhesive compositions of this invention are curable compounds, meaning that they are capable of polymerization, with or without crosslinking. As used in this specification, to cure will mean to polymerize, with or without crosslinking. Cross-linking, as is understood in the art, is the attachment of two polymer chains by bridges of an element, a molecular group, or a compound, and in general will take place upon heating or irradiation. As cross-linking density is increased, the properties of a material can be changed from thermoplastic to thermosetting.

The adhesive compositions will further comprise at least one free-radical initiator, which is defined to be a chemical species that decomposes to a molecular fragment having one or more unpaired electrons, highly reactive and usually short-lived, which is capable of initiating a chemical reaction by means of a chain mechanism. The free-radical initiator will be present in an amount of 0.1 to 10 percent, preferably 0.1 to 3.0 percent, by weight of the organic compounds (excluding any filler). The free radical curing mechanism gives a fast cure and provides the composition with a long shelf life before cure. Preferred free-radical initiators include peroxides, such as butyl peroctoates and dicumyl peroxide, and azo compounds, such as 2,2'-azobis(2-methyl-propanenitrile) and 2, 2'-azobis (2-methyl-butanenitrile).

Alternatively, the adhesive compositions may contain a photoinitiator in lieu of the free-radical initiator, and the curing process may then be initiated by UV radiation. The photoinitiator will be present in an amount of 0.1 to 10 percent, preferably 1 to 5.0 percent, by weight of the organic compounds (excluding any filler). In some cases, both photoinitiation and thermal initiation may be desirable. For example, the curing process can be started by UV irradiation, and in a later processing step, curing can be completed by the application of heat to accomplish a free-radical cure.

In general, these compositions will cure within a temperature range of 80-200° C., and curing will be effected within a length of time of less than one minute to 60 minutes. As will be understood, the time and temperature curing profile for each adhesive composition will vary, and different compositions can be designed to provide the curing profile that will be suited to the particular industrial manufacturing process.

Suitable conductive fillers for the adhesives are silver, copper, gold, palladium, platinum. In some circumstances, non-conductive fillers may be needed, for example to adjust rheology, such as, alumina, silica, and teflon.

Other additives, such as adhesion promoters, in types and amounts known in the art, may also be added.

These compositions will perform within the commercially acceptable range for die attach adhesives. Commercially acceptable values for die shear for the adhesives on a 80×80 mil$^2$ silicon die are in the range of greater than or equal to 1 kg at room temperature, and greater than or equal to 0.5 kg at 240° C., and for warpage for a 500×500 mil$^2$ die are in the range of less than or equal to 70 μm at room temperature.

A typical synthetic scheme for making these materials comprises reacting maleic anhydride with an amino acid to form an amic acid adduct. The adduct is dehydrated and closed into the maleimide ring with carboxyl functionality. The carboxyl functionality on the maleimide is further reacted with the hydroxyl groups on 1,3,5-tris(2-hydroxyethyl)cyanuric acid to give the maleimide resin with cyanurate core.

Formation of the amic acid adduct occurs through the reaction of maleic anhydride in a suitable solvent, such as acetonitrile, with a molar equivalent of an amino acid, such as 6-aminocaprioc acid or beta-alanine, in acetic acid. The reaction occurs at room temperature, generally over three to four hours. The product is collected by filtration, washed with cold acetonitrile and dried to give the amic acid adduct. The amic acid adduct is mixed with triethylamine in toluene and heated (within the range of 110° C. to 150° C.) for several hours to cause dehydration and ring closure. The water produced by the reaction is collected and removed, the organic solvent evaporated off, and the pH adjusted to 2 with 2M HCl to neutralize the product. The resultant maleimide with carboxyl functionality is extracted with ethyl acetate, dried over MgSO₄, and the solvent evaporated. Exemplary maleimides include 6-maleimidocaproic acid and 3-maleimidopropionic acid.

is removed. The mixture is filtered, and the filtrate washed in triethylamine for one hour, followed by washing three times with a solution of 20% NaCl. The organics are collected, dried over silica, and the solvent evaporated to give the maleimide with cyanurate core. In these products there is an ester functionality linking the arms and the cyanurate core.

In addition to the compound disclosed in Example 1, the above method can be used to make a variety of compounds having different levels of substitution and lengths of the arms capped with the maleimide. The following are additional exemplary compounds.

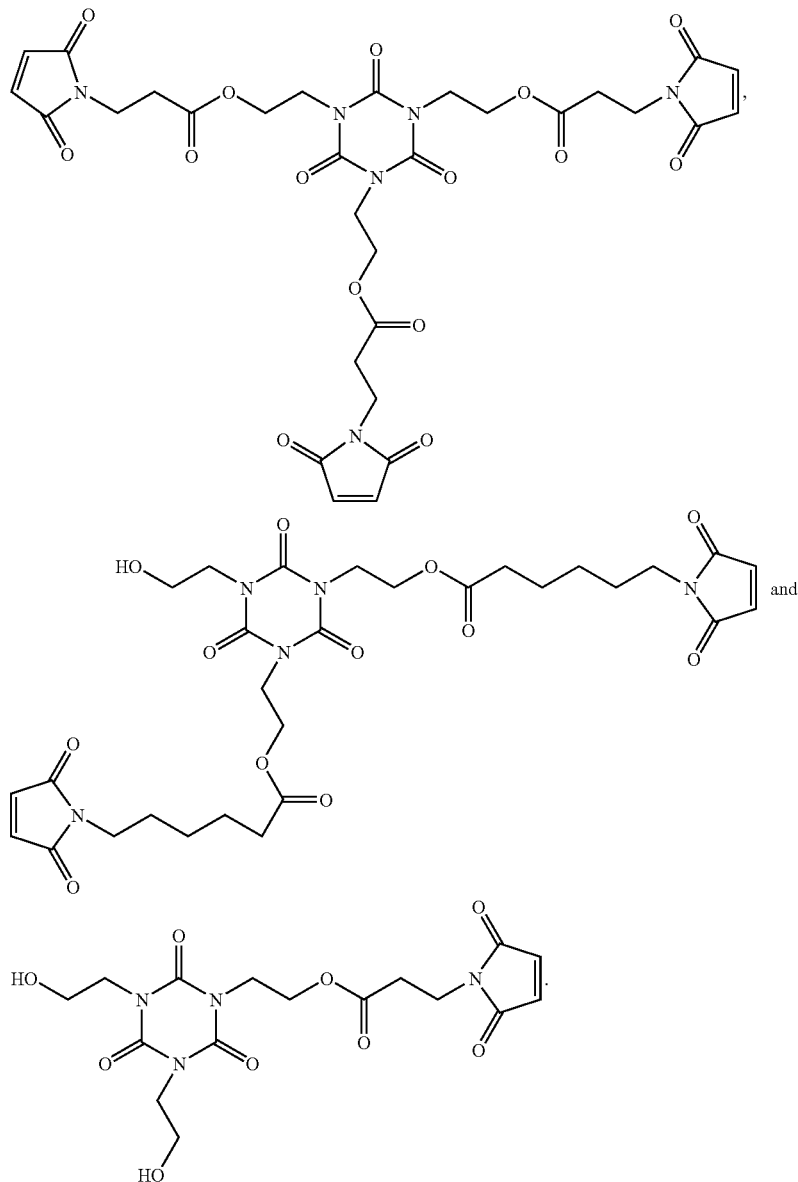

To form the maleimide with isocyanurate core, the maleimide is reacted with 1,3,5-tris(2-hydroxyethyl)cyanuric acid in sulfuric acid and a suitable solvent, such as toluene. The molar equivalents are adjusted to give the desired level of substitution on the cyanurate. The reaction is heated to reflux until the theoretical amount of water produced by the reaction In another embodiment, the maleimides with cyanurate core contain carbamate functionality. A synthetic scheme for preparing these compounds comprises making the acid chloride analog of the maleimide with carboxyl functionality, reacting the acid chloride with sodium azide to form a maleimide with isocyanate functionality, and finally reacting the isocyanate with the 1,3,5-tris(2-hydroxyethyl)cyanuric acid.

The maleimide with carboxyl functionality is reacted with an excess of thionyl chloride under typical conditions (for example, 50° C. for three hours) to form the acid chloride. Any remaining thionyl chloride is distilled off to leave the maleimide with acid chloride functionality. The maleimide with acid chloride functionality is added slowly and dropwise to a chilled (10° C.) solution of sodium azide in water, toluene, and a catalytic amount of benzyltriethyl-ammonium chloride, previously prepared with vigorous stirring. Stirring of the solution is continued over a few hours, initially at about 15° C. and then at about 20° C. The organic phase is separated off, washed with 2N aqueous sodium bicarbonate solution and with water, dried with MgSO₄, and filtered. The filtrate is heated slowly to the reflux temperature, and reflux maintained until the evolution of nitrogen has ceased. The solution is heated under reflux for a further 30 minutes and, after cooling, is concentrated using a rotary evaporator. The residue is distilled under a high vacuum to produce the maleimide with isocyanate functionality.

Depending on the level of substitution on the cyanurate core desired, one to three mole equivalents of maleimide with isocyanate functionality (per 1,3,5-tris(2-hydroxyethyl)cyanuric acid) is solvated in toluene, the solution placed under nitrogen and heated to 70° C. One mole equivalent of 1,3,5-tris(2-hydroxyethyl)cyanuric acid dissolved in toluene is added to the isocyanate solution over several minutes, and the resulting mixture heated for an additional three to four hours at 70° C. After the reaction is allowed to cool to room temperature, the mixture is washed with distilled water three times, the organic layer isolated and dried and over MgSO₄, filtered, and the solvent removed in vacuo to give the product.

Exemplary compounds prepared by the above method include

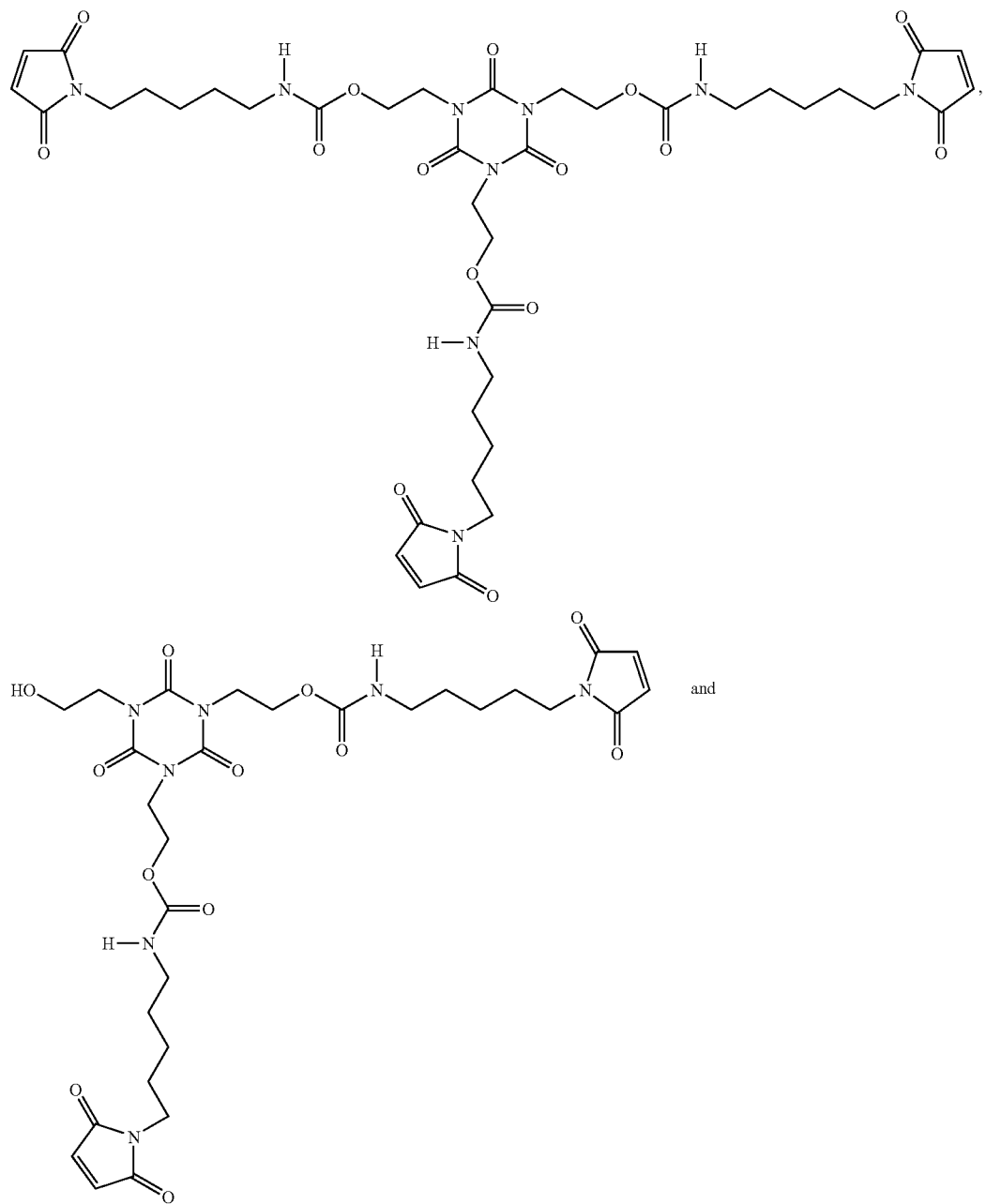

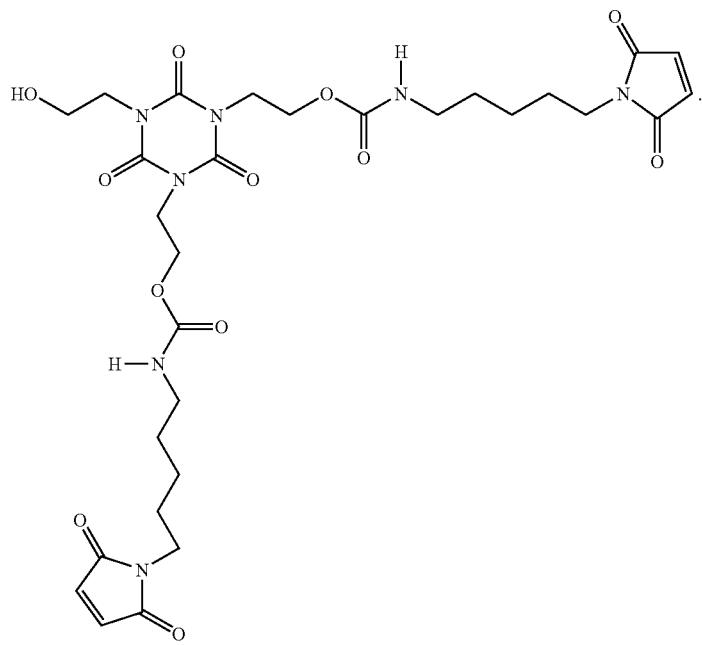

In another embodiment, the maleimides with cyanurate core containing carbamate functionality can be prepared starting with the isocyanate functionality on the cyanurate, as for example, in the starting compound Desmodur N3300, commercially available from Bayer, shown here:

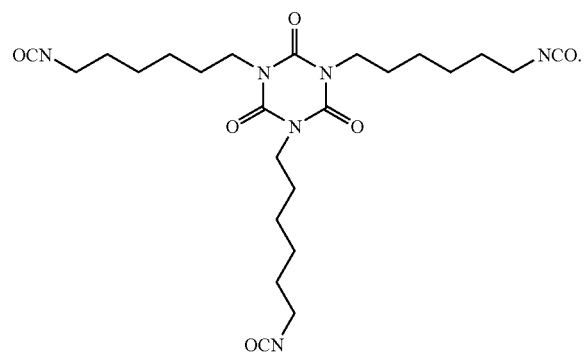

One mole equivalent of the starting compound is solvated in toluene, placed under nitrogen, and the solution heated to 70° C. Depending on the level of substitution desired, one to three molar equivalents of N-alkylol-maleimide (prepared according to J. Bartus, W. L. Simonsick, and O. Vogl, *J.M.S.-Pure Appl. Chem.*, A36(3), 355, 1999) dissolved in toluene, is then added to the isocyanate solution over several minutes, and the resulting mixture heated for an additional three to four hours at 70° C. The reaction is allowed to cool to room temperature, the mixture washed with distilled water three times, the organic layer isolated, dried over MgSO$_4$, filtered, and the solvent removed in vacuo to give the product. An exemplary compound prepared by this method has the structure:

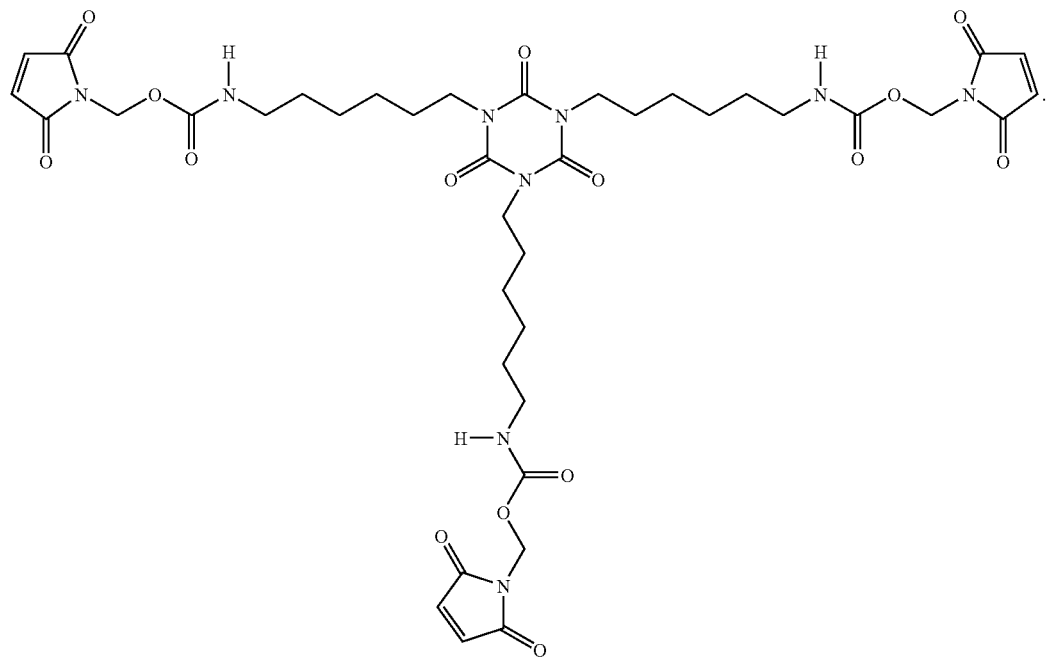

EXAMPLES

Example 1

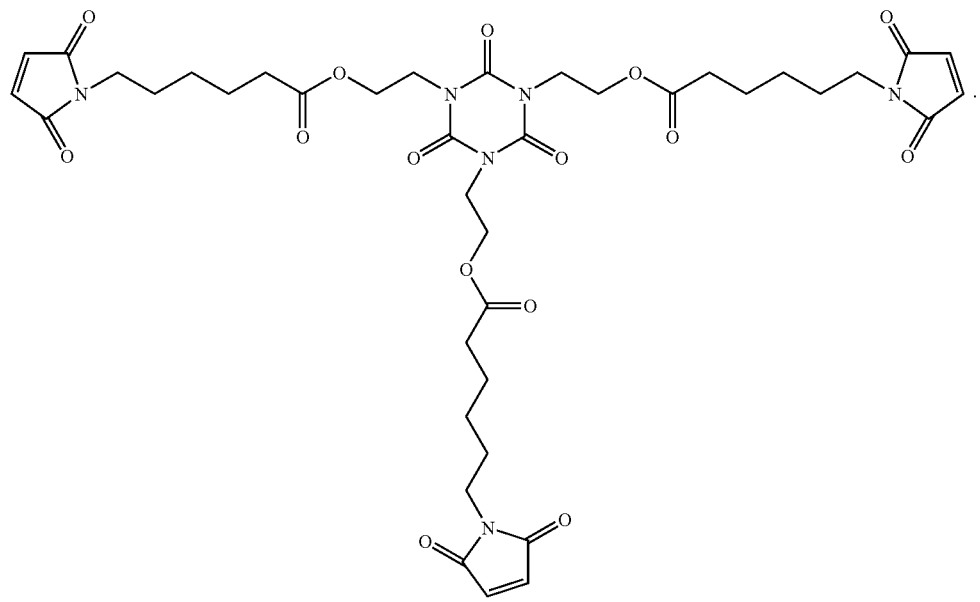

Formation of the amic acid adduct, 6-maleimidocaproic acid. A solution of one mole equivalent of maleic anhydride in acetonitrile is added to a one mole equivalent of 6-aminocaprioc acid in acetic acid. The mixture is allowed to react for three hours at room temperature. The formed white crystals are filtered off, washed with cold acetonitrile and dried to produce the amic acid adduct. Amic acid is mixed with triethylamine in toluene. The mixture is heated to 130° C. for two hours and water is collected in Dean-Stark trap. The organic solvent is evaporated and the 2M HCL to reach pH 2. Extraction with ethyl acetate and drying over $MgSO_4$ followed by evaporating of the solvent gave 6-maleimidocaproic acid (MCA).

Formation of the cyanurate: A one liter flask was charged with 1,3,5-tris(2-hydroxyethyl)cyanuric acid (25.00 g, 96 mmol), 6-maleimidocaproic acid (60.65 g, 287 mmol), sulfuric acid (1.00 g, 10 mmol), and toluene (400 mL). The reaction vessel was equipped with an overhead stirrer, Dean-Stark trap, and condenser. The contents were heated to 115° C. and allowed to reflux. The reaction was continued until the calculated amount of water was achieved. After the reaction flask cooled to room temperature, the mixture was filtered. Triethylamine (12.4 g, 123 mmol) was added to the flask and stirred for one hour. After this interval, the mixture was washed with 20% NaCl solution (3×400 mL). The organics were collected and silica gel (50 g) was added, stirred for one hour, filtered, and the solvent was removed in vacuo to afford a clear, but slightly yellow liquid. The yield was approximately 50%. The viscosity of this trifunctional maleimide resin was 26,000 cPs at 50° C. while the volatility was determined to be 0.12% at 200° C., based on TGA analysis. The NMR is attached as FIG. 1.

Example 2

A formulation of resins comprising 10 parts by weight of a bismaleimide resin, 10 parts by weight of an epoxy resin, 10 parts by weight an acrylate resin and 15 parts by weight of ethylene glycol diethyl methacrylate, with effective amounts of curing agent and adhesion promoter, was blended with 45% by weight silver flake. To this formulation was added 2.5 parts by weight of the compound from Example 1, and in a control, 2.5 parts by weight of an acrylate compound having a cyanuarate core with the following structure:

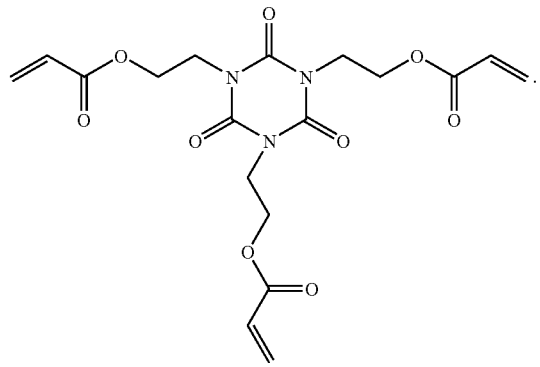

The control formulation and the formulation containing the maleimide with cyanurate core were tested for volume resistivity and for die shear strength. The volume resistivity for each formulation was about 0.00002 ohm-cm. The adhesive strength of each formulation was tested as die shear strength using a 500×500 mil silicon die on a silver coated leadframe at 260° C. after a two minute cure at 200° C. The inventive maleimide formulation had a superior die shear strength of 0.36 Kg compared with the control formulation, which had a die shear strength of 0.25 Kg.

What is claimed is:

1. A compound having the structure

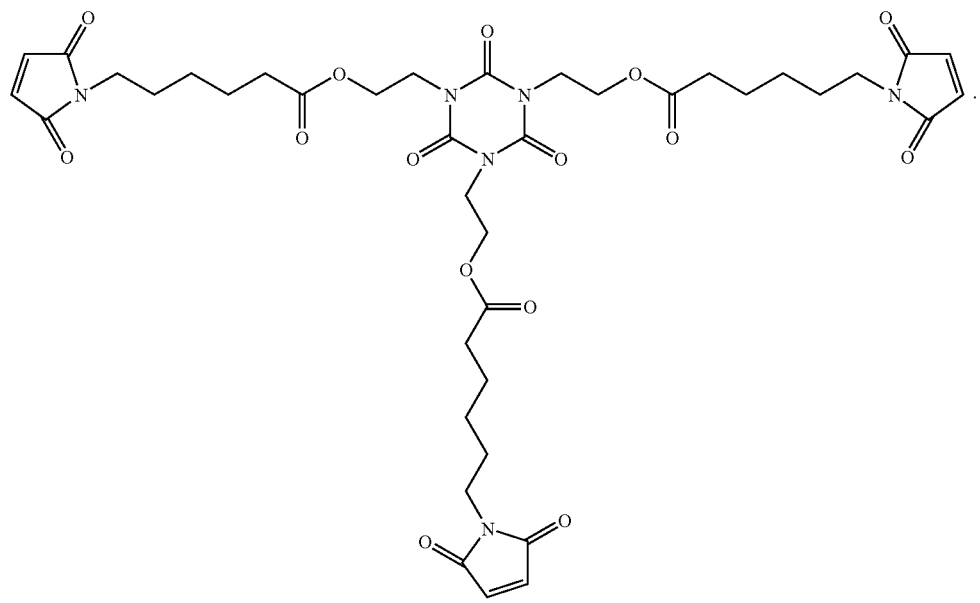

2. A compound having the structure
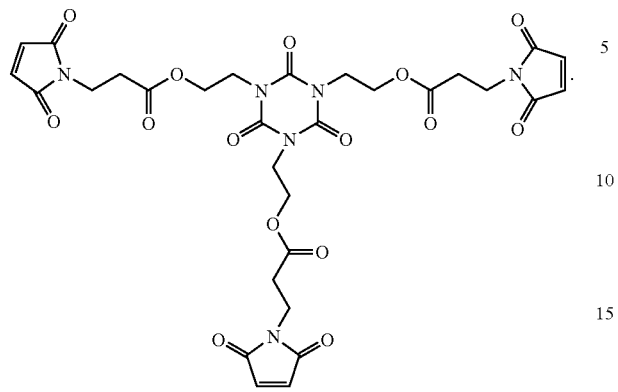
3. A compound having the structure
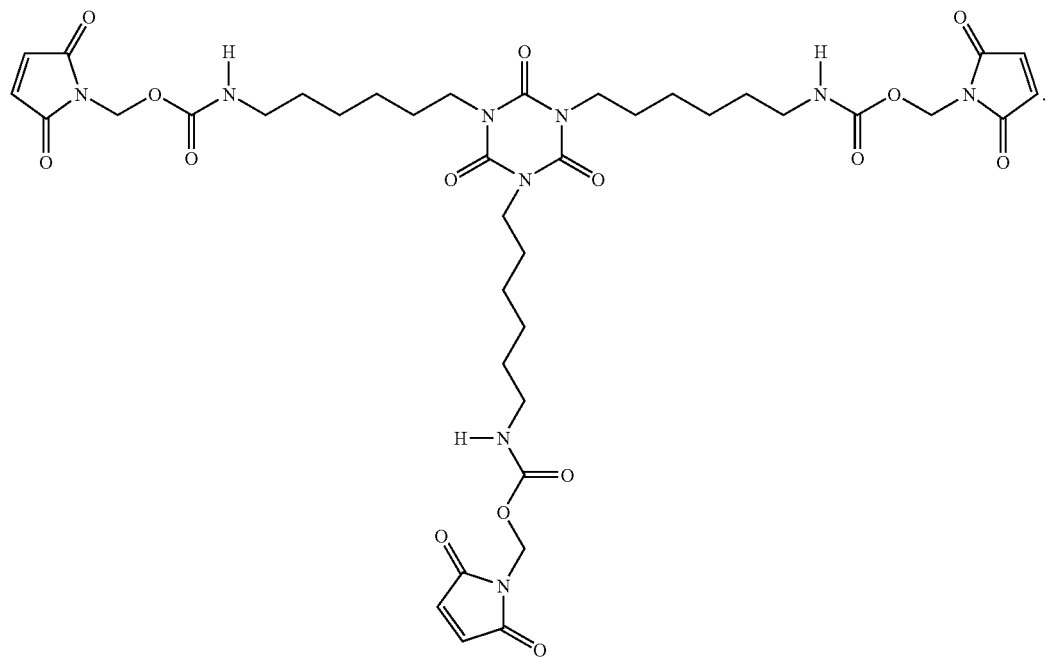
* * * * *